United States Patent
Guerra

(10) Patent No.: US 7,176,331 B2
(45) Date of Patent: Feb. 13, 2007

(54) METHOD OF MAKING FLUORINATED VINYL ETHERS

(75) Inventor: Miguel Antonio Guerra, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/171,966

(22) Filed: Jun. 30, 2005

(65) Prior Publication Data

US 2007/0004938 A1  Jan. 4, 2007

(51) Int. Cl.
   *C07C 309/81* (2006.01)
(52) U.S. Cl. .................. 562/825; 568/615; 568/616; 568/685
(58) Field of Classification Search ............ 568/32, 568/615, 616, 685; 562/825
   See application file for complete search history.

(56) References Cited

U.S. PATENT DOCUMENTS

| | | | |
|---|---|---|---|
| 3,291,843 A | 12/1966 | Fritz et al. | |
| 4,358,412 A | 11/1982 | Ezzell et al. | |
| 4,414,159 A | 11/1983 | Resnick | |
| 4,772,756 A | 9/1988 | Bornengo et al. | |
| 5,391,796 A | 2/1995 | Farnham | |
| 5,902,908 A | 5/1999 | Morita et al. | |
| 6,482,979 B1 | 11/2002 | Hintzer et al. | |
| 2004/0176636 A1 | 9/2004 | Hoshi et al. | |

OTHER PUBLICATIONS

Conroy, Patrick J., http://www.rpi.edu/dept/chem-eng/Biotech-Environ/IMMOB/fluidized-bed.htm, 1997.*

* cited by examiner

*Primary Examiner*—Rosalynd Keys

(57) ABSTRACT

The present application provides a process to produce fluorinated vinyl ether by reacting a 2-alkoxypropionyl fluoride with a metal carbonate under anhydrous conditions in a stirred bed reactor at a temperature above the decarboxylation temperature of an intermediate carboxylate to produce a fluorinated vinyl ether. The process is carried out in the absence of solvent. With the process described, fluorinated vinyl ether of a high purity can be obtained in a high throughput manner.

22 Claims, No Drawings

METHOD OF MAKING FLUORINATED VINYL ETHERS

TECHNICAL FIELD

This invention relates to fluorinated vinyl ethers and methods of making fluorinated vinyl ethers.

BACKGROUND

Fluorinated vinyl ethers are known as raw materials that may be copolymerized with other fluorinated monomers to produce industrially useful polymeric materials. For example, fluorinated vinyl ethers can be copolymerized with other monomers to form materials such as PFA (a copolymer with tetrafluoroethylene), perfluorinated rubber materials, and modified PTFE.

Various examples of methods for fluorinated vinyl ether synthesis are available. These methods include reacting a 2-alkoxypropionyl fluoride in a stationary bed of a metal carbonate, a tubular reactor filled with dried metal carbonate and equipped with a screw blade running through the tube, and a fluidized bed of metal carbonate. Furthermore, available methods include a two-step process wherein the reactants are mixed below the decomposition temperature of an intermediate and in a second step, the temperature is raised to yield a fluorinated vinyl ether. This two step slow heating process may also be carried out in the presence of a solvent and/or a catalytic amount of N,N-dimethylformamide. Solvent based methods are widely used, despite their tendency to yield a larger proportion of unwanted side products (e.g., the HF adduct of the fluorinated vinyl ether) than comparable solvent free methods.

Other methods have utilized 3-substituted 2-alkoxypropionyl fluorides (wherein the substituents in the 3-position include Cl, Br or I). These are decarboxylated to yield the vinyl ether in preference over the five or six membered ring products (which are favored when the 2-alkoxypropionyl fluorides are perfluorinated in the 3-position). These reactions are generally carried out in tetraglyme as a reaction solvent.

Further examples have dispatched with the use of metal carbonates and instead react siloxanes with 2-alkoxypropionyl fluorides or carboxylic anhydrides to yield fluorovinyl ethers.

SUMMARY

It is recognized herein that a need exists for a high throughput preparation process for fluorinated vinyl ethers from 2-alkoxypropionyl fluoride. In particular, such processes would advantageously minimize undesirable reaction byproducts, such as the HF adduct of the fluorinated vinyl ether. Furthermore, process considerations of cost and environmental disposal favor solvent free methods for the preparation of fluorinated vinyl ethers. Finally, the process described herein is preferred over fluidized bed methods because, for instance, fluidized bed methods present additional process variables that add expense and risk to their implementation.

Briefly, the present description is directed to a process for the high throughput preparation of fluorinated vinyl ethers from 2-alkoxypropionyl fluoride and metal carbonate. The process comprises placing a metal carbonate in a stirred bed reactor under anhydrous conditions. The process further comprises feeding a 2-alkoxypropionyl fluoride into the stirred bed reactor and maintaining the metal carbonate at a temperature above the decarboxylation temperature of an intermediate carboxylate to produce a fluorinated vinyl ether. The process described herein is carried out in the absence of solvent.

Other features and advantages of the process will be apparent from the following detailed description and the claims. The above summary of principles of the disclosure is not intended to describe each illustrated embodiment or every implementation of the process. The following details more particularly exemplify certain preferred embodiments utilizing the principles disclosed herein.

DETAILED DESCRIPTION

The present invention is a process for the high throughput preparation of fluorinated vinyl ethers from fluorinated 2-alkoxypropionyl fluoride. Suitable 2-alkoxypropionyl fluoride feeds include those given by the general formula $X-(O-Y)_a-O-CF(CF_3)COF$ wherein X is selected from the group consisting of $C_nF_{2n+1}$ wherein n is 1 to 10, $FSO_2(C_mF_{2m})$ wherein m is 1 to 10, and $FCO(C_dF_{2d})$ wherein d is 1 to 10; Y is selected from the group consisting of $C_pF_{2p}$ wherein p is 1 to 10, and $CF(CF_3)CF_2$; and a is 0 to 10. In particular, suitable 2-alkoxypropionyl fluorides include: $CF_3-O-CF(CF_3)COF$, $CF_3CF_2-O-CF(CF_3)COF$, $CF_3CF_2CF_2-O-CF(CF_3)COF$, $CF_3-O-CF_2CF_2CF_2-O-CF(CF_3)COF$, $CF_3CF_2-O-CF_2-O-CF(CF_3)COF$, $CF_3-O-CF_2CF_2-O-CF_2CF_2-O-CF(CF_3)COF$, $CF_3CF_2-O-CF_2CF_2-O-CF_2CF_2-O-CF(CF_3)COF$, $CF_3CF_2CF_2-O-[CF(CF_3)CF_2-O]_aCF(CF_3)COF$ (wherein a is as defined above), $FSO_2CF_2CF_2CF_2CF_2-O-CF(CF_3)COF$, and $FCOCF_2CF_2CF_2CF_2-O-CF(CF_3)COF$. The 2-alkoxypropionyl fluoride compounds may be a liquid at atmospheric conditions (298° C., 1 atm), although 2-alkoxypropionyl fluoride compounds that are in the gas phase at atmospheric conditions are also suitable.

Metal carbonates suitable for the present process include sodium carbonate, potassium carbonate, and combinations thereof. In one aspect of the process, the metal carbonates may be anhydrous. Any suitable method of preparing or providing anhydrous metal carbonate may be used in the present process. Anhydrous metal carbonates may be provided, for instance, by heating the metal carbonate to 250° C. while flowing an inert gas, such as nitrogen or argon, over or through the metal carbonate for at least two hours. This may be done at atmospheric pressure or under reduced pressure. Particularly suited to the present process, an anhydrous metal carbonate as described above may be prepared in a stirred reactor. The stirring of the reactor allows for continuous exposure of new surfaces of the metal carbonate and promotes water loss. Suitable metal carbonates include powdered metal carbonates.

Stirred bed reactors are suitable for use in the process described herein. While no particular rate of stirring or stirring method is required, one should be mindful of the fact that the chemical reaction involved in the process described herein is stoichiometric. That is, for each mole of 2-alkoxypropionyl fluoride converted to fluorinated vinyl ether, one mole of metal carbonate is consumed. As such, it is important that the stirring method and equipment used to stir the metal carbonate bed should be chosen so as to continuously expose unreacted metal carbonate to the 2-alkoxypropionyl fluoride. By continuously exposing unreacted metal carbonate, the process may, for instance, reduce the amount of unreacted 2-alkoxypropionyl fluoride, increase the rate of reaction, minimize unwanted side reactions, or some combination thereof.

In one aspect, the process described herein comprises placing a metal carbonate into a stirred bed reactor. The stirred bed reactor may be of any design convenient for carrying out the process described herein. In another aspect, the process further comprises maintaining the metal carbonate at a temperature above the decarboxylation temperature of an intermediate carboxylate formed when the 2-alkoxypropionyl fluoride is contacted with the metal carbonate. Preferably, the stirred bed reactor should be capable of achieving a wide range of temperatures. A suitable temperature range includes 25 to 500° C., more suitably 100 to 300° C. Furthermore, the stirred bed reactor design should allow for feeding a 2-alkoxypropionyl fluoride into the reactor while stirring. The 2-alkoxypropionyl fluoride may be fed in as a liquid or gas. The 2-alkoxypropionyl fluoride may be fed into the stirred bed reactor while maintaining the metal carbonate at a temperature above the decarboxylation temperature of an intermediate carboxylate.

By feeding the 2-alkoxypropionyl fluoride into the stirred bed reactor at a temperature above the decarboxylation temperature of an intermediate carboxylate, a fluorinated vinyl ether is produced. Without wishing to limit the scope of the present description, the reaction sequence is believed to be the following:

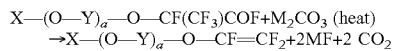

X—(O—Y)$_a$—O—CF(CF$_3$)COF+M$_2$CO$_3$ (heat)
→X—(O—Y)$_a$—O—CF═CF$_2$+2MF+2 CO$_2$ wherein X is selected from the group consisting of C$_2$F$_{2n+1}$ wherein n is 1 to 10, FSO$_2$(C$_m$F$_{2m}$) wherein m is 1 to 10, and FCO(C$_d$F$_{2d}$) wherein d is 1 to 10; Y is selected from the group consisting of C$_p$F$_{2p}$ wherein p is 1 to 10, and CF(CF$_3$)CF$_2$; a is 0 to 10; and M is selected from sodium or potassium.

The process described herein takes place in the absence of solvent. Thus, the process described eliminates the need for aprotic solvents, such as the glyme solvents, that are believed to lead to undesirable byproducts such as the hydride adduct. The hydride adduct may be, for instance, a compound having the formula X—(O—Y)$_a$—O—CFH—CF$_3$, wherein X, Y and a are defined above. The hydride adduct is believed to result from residual moisture from the solvents. The absence of solvent in the process described herein also eliminates potential problems caused by foaming which may occur during the decarboxylation of 2-alkoxypropionyl fluorides by metal carbonates in the presence of solvent.

The process described herein also provides the advantage of a single-pot synthesis. Particularly, prior art processes involved a two-step process of titrating a 2-alkoxypropionyl fluoride with an aqueous caustic followed by phase splitting the concentrated lower aqueous fluorinated metal acid salt, then vacuum drying over time to remove moisture, followed by raising the temperature above the decarboxylation temperature, only then to yield the fluorinated vinyl ether. In particular, the intermediate fluorinated metal salts of the prior art processes can be hard to stir. The process described herein may eliminate such stirring problems by not building up, or by not generating to any substantial degree, the intermediate fluorinated metal salt. To this end, the metal carbonate may be present in excess mol % over the 2-alkoxypropionyl fluoride used. Thus, the bulk of the solids in the reactor will be the excess metal carbonate and metal fluoride byproduct, which are much easier to stir and do not present the processing challenges presented by the intermediate fluorinated metal salts of the prior art processes.

Vinyl ethers that can be produced by the present method include, for example, those given by the general formula X—(O—Y)$_a$—O—CF═CF$_2$ wherein X is selected from the group consisting of C$_n$F$_{2n+1}$ wherein n is 1 to 10, FSO$_2$(C$_m$F$_{2m}$) wherein m is 1 to 10, and FCO(C$_d$F$_{2d}$) wherein d is 1 to 10; Y is selected from the group consisting of C$_p$F$_{2p}$ wherein p is 1 to 10, and CF(CF$_3$)CF$_2$; and a is 0 to 10. Particular vinyl ethers that can be produced by the present method include, for example, CF$_3$—O—CF═CF$_2$, CF$_3$CF$_2$—O—CF═CF$_2$, CF$_3$CF$_2$CF$_2$—O—CF═CF$_2$, CF$_3$—O—CF$_2$CF$_2$CF$_2$—O—CF═CF$_2$, CF$_3$CF$_2$—O—CF$_2$—O—CF═CF$_2$, CF$_3$—O—CF$_2$CF$_2$—O—CF$_2$CF$_2$—O—CF═CF$_2$, CF$_3$CF$_2$—O—CF$_2$CF$_2$—O—CF$_2$CF$_2$—O—CF═CF$_2$, CF$_3$CF$_2$CF$_2$—O—[CF(CF$_3$)CF$_2$—O]$_a$CF═CF$_2$ (wherein a is as defined above), FSO$_2$CF$_2$CF$_2$CF$_2$CF$_2$—O—CF═CF$_2$, and CH$_3$OCOCF$_2$CF$_2$CF$_2$CF$_2$CF$_2$—O—CF═CF$_2$.

The process may yield a vinyl ether almost exclusively, producing a hydride adduct, preferably in less than 0.5 mol %. By eliminating the solvent from the process described herein, and performing the process under anhydrous conditions, the present process may yield a vinyl ether product and less than 0.5 mol % of the hydride adduct.

Even though the process may yield less than 0.5 mol % of the hydride adduct, the process may further comprise isolating the desired vinyl ether from reaction impurities. The particular method of isolation is not vitally important, and any suitable separation technique generally recognized by those of skill in the art will suffice. Examples of isolation methods particularly suitable for the present process may comprise, for instance, distillation of the reaction mixture or fractionalization of the reaction mixture.

The process may further comprise collecting the fluorinated vinyl ether. While the collection technique is not vital, it may comprise, for instance, condensation of gaseous fluorinated vinyl ether product or distillation of liquid fluorinated vinyl ether product. While the process described herein may be carried out at atmospheric pressure, it may also be run under reduced pressure. When reduced pressure is used, suitable collection techniques may include cold temperature trapping of fluorinated vinyl ether products.

The feed rate of 2-alkoxypropionyl fluoride into the reactor may be controlled to optimize the yield of fluorinated vinyl ether. Since the reaction is stoichiometric in nature, the feed rate may be adjusted throughout the reaction to accommodate the decreasing amount of unreacted metal carbonate in the stirred reactor. In connection with the goal of maximizing the contact time between the metal carbonate and the 2-alkoxypropionyl fluoride added, the stir rate may also be optimized throughout the process described herein. In particular, a combination of feed rate and stir rate adjustments may be made to provide for optimum reaction conditions. The feed rate will depend, for instance, on the size of the stirred bed reactor, the amount of metal carbonate used, the rate of stirring, and the proportion of unreacted metal carbonate left in the stirred bed reactor. A feed rate above or below the ranges mentioned herein is contemplated and may be chosen based upon the particular details of the reaction conditions and variables, such as those mentioned herein. In one embodiment, the process may further comprise adjusting the feed rate of the 2-alkoxypropionyl fluoride to a working feed rate, wherein the working feed rate is the rate at which 95 mol % of the 2-alkoxypropionyl fluoride is converted to the fluorinated vinyl ether.

In another aspect, the temperature of the reactor may be controlled to optimize the yield of fluorinated vinyl ether. The particular combination of a certain 2-alkoxypropionyl fluoride and a certain metal carbonate may require adjusting the temperature of the reactor to optimize the reaction conditions. Such optimization may be based upon, for instance, maximizing the rate of reaction, minimizing unwanted side reactions (such as, for instance, the formation of the hydride adduct), minimizing the thermal decomposition of the 2-alkoxypropionyl fluoride, and combinations thereof.

Recognizing that it might not be possible to optimize all of the individual reaction variables simultaneously, it should be recognized that one may adjust any combination thereof based upon the desired output of the particular embodiment practices of the process described herein.

In yet another aspect, the process may further comprise recycling unreacted 2-alkoxypropionyl fluoride back into the reactor. While it is preferred that the 2-alkoxypropionyl fluoride is quantitatively converted into the corresponding fluorinated vinyl ether, some unreacted 2-alkoxypropionyl fluoride may exit the stirred bed reactor in a product stream. When this is the case, it may be desirable to recycle the unreacted 2-alkoxypropionyl fluoride back into the reactor for conversion into the desired fluorinated vinyl ether.

Various modifications and alterations of this invention will become apparent to those skilled in the art without departing from the scope and principles of the process described herein, and it should be understood that this process is not to be unduly limited to the illustrative embodiments set forth hereinabove and in the Examples below.

EXAMPLES

Unless otherwise noted, all reagents were obtained or are available from Aldrich Chemical Co., Milwaukee, Wis., or may be synthesized by known methods. The pump used was an ISO-100 Isocratic Pump from Chrom Tech, Inc., Apply Valley, Minn. with flow rates from 0.01 to 10 ml/min.

Example 1

Reacting $K_2CO_3$ and Perfluoromethoxypropoxyproponyl Fluoride

A 2-L resin flask was equipped with a mechanical stirrer, distillation overhead and a 0.125 inch stainless steel feed line that went to the bottom of the flask. Potassium carbonate powder (171 g, 1.24 mol), was charged and the reactor was heated to 240° C. with a slight nitrogen sweep of the head space for 2 hours with slow stirring. After drying the sodium carbonate, the nitrogen was stopped and addition of perfluoromethoxypropoxyproponyl fluoride (prepared from the acid fluoride described in U.S. Pat. No. 6,482,979 reacted with hexafluoropropylene oxide described in U.S. Pat. No. 4,749,526) $CF_3$—O—$CF_2CF_2CF_2$—O—$CF(CF_3)COF$ (205 g, 0.5 mol) was added through the feed line over one hour. During the addition of the acid fluoride, $CO_2$ gas was produced and 152 g of perfluoromethoxypropyl vinyl ether $CF_3$—O—$CF_2CF_2CF_2$—O—$CF$=$CF_2$ was collected downstream for an 89.4% crude yield. Fluorine and proton NMR identified the compound at 98% conversion giving a final yield of 87.6% (0.5% yield of hydride byproduct was made, $CF_3$—O—$CF_2CF_2CF_2$—O—$CFHCF_3$).

Example 2

Reacting $Na_2CO_3$ and Perfluoromethoxypropoxypropionyl Fluoride

The reaction was carried out as in Example 1, except that sodium carbonate powder (92 g, 0.87 mol) was used and 198 g, 0.5 mol of perfluoromethoxypropoxypropionyl fluoride $CF_3$—O—$CF_2CF_2CF_2$—O—$CF(CF_3)COF$ was added over 45 minutes at 280° C. giving 151 g of crude product with 76% conversion for a final yield of 69%. Fluorine and proton NMR identified the compound. (0.5% yield of hydride byproduct was made, $CF_3$—O—$CF_2CF_2CF_2$—O—$CFHCF_3$).

Example 3

Reacting $Na_2CO_3$ and Perfluorobutoxy Sulfonyl Fluoride Propionyl Fluoride

The reaction was carried out as in Example 1, except that sodium carbonate powder (60 g, 0.57 mol) was used and 100 g, 0.224 mol of perfluorobutoxy sulfonyl fluoride propionyl fluoride $FSO_2CF2CF_2CF_2CF_2$—O—$CF(CF_3)COF$ (prepared as described in U.S. Pat. No. 6,624,328) was added over 1 hour at 250° C. giving 77 g of crude product with 74% conversion of acid fluoride to vinyl ether, $FSO_2CF2CF_2CF_2CF_2$—O—$CF$=$CF_2$, with low levels of hydride detected by fluorine and proton NMR. Un-reacted acid fluoride can be recycled.

Example 4

Reacting $K_2CO_3$ and Perfluorobutoxy Sulfonyl Fluoride Propionyl Fluoride

The reaction was carried out as in Example 3 except that potassium carbonate (83 g, 0.6 mol) was used and 145 g, 0.33 mol of perfluorobutoxy sulfonyl fluoride propionyl fluoride $FSO_2CF2CF_2CF_2CF_2$—O—$CF(CF_3)COF$ was added over 30 minutes at 250° C. giving 90 g of crude product with an 18% conversion of acid fluoride to vinyl ether, with low level of hydride detected by fluorine and proton NMR.

Comparative Example 1

Solvent Based Reaction

To a 40-L reactor was charged sodium carbonate (3600 g, 34 mol) and 8.2 kg of diglyme. The slurry was stirred and vacuum heated to distill over some diglyme to dry the system. Nitrogen was used to break vacuum and the reactor temperature was set to 78° C. Addition of perfluoromethoxypropoxypropionyl fluoride $CF_3$—O—$CF_2CF_2CF_2$—O—$CF(CF_3)COF$ (8200 g, 20.6 mol) over two hours at this temperature gave off $CO_2$ gas. After holding for one hour the temperature was incrementally raise to minimize foaming and set to a final temperature of 145° C. This resulted in decarboxylation producing $CO_2$ and distilling out perfluoromethoxypropyl vinyl ether $CF_3$—O—$CF_2CF_2CF_2$—O—$CF$=$CF_2$. The product was neutralized, water washed and distilled to recover 3060 g for a 45% final yield confirmed by GCMS. (14% yield of hydride byproduct was made, $CF_3$—O—$CF_2CF_2CF_2$—O—$CFHCF_3$).

Comparative Example 2

Two-Step Process

A 1-L round bottom flask was equipped with a mechanical stirrer, addition funnel and condenser. A 33% caustic solution was made with potassium hydroxide (154 g, 2.3 mol) and 312 g of water. Addition of perfluoromethoxypropoxypropionyl fluoride $CF_3$—O—$CF_2CF_2CF_2$—O—CF($CF_3$)COF (464 g, 1.16 mol) over one hour was exothermic. The lower fluorochemical phase of 617 g had 74% solids for a 90% yield of fluorochemical acid salt. A 100 g charge of the aqueous fluorochemical acid salt was placed in a 500 ml round bottom flask and vacuum dried at 152° C. for four hours at 15 mm. After all the water had been removed the vacuum was broken and the solids heated to 275° C. Decarboxylation produced $CO_2$ and 33.6 g perfluoromethoxypropyl vinyl ether $CF_3$—O—$CF_2CF_2CF_2$—O—CF=$CF_2$ for a 59.4% final yield. The product was confirmed by GCMS. (6.2% yield of hydride byproduct was made, $CF_3$—O—$CF_2CF_2CF_2$—O—$CFHCF_3$).

I claim:

1. A process for the high throughput preparation of fluorinated vinyl ethers from fluorinated 2-alkoxypropionyl fluoride and metal carbonate comprising:
   a) placing a metal carbonate in a stirred bed reactor under anhydrous conditions; and
   b) feeding a 2-alkoxypropionyl fluoride into the stirred bed reactor while stirring the metal carbonate and maintaining the metal carbonate at a temperature above the decarboxylation temperature of an intermediate carboxylate to produce a fluorinated vinyl ether
wherein the process is carried out in the absence of a solvent.

2. The process according to claim 1 wherein a hydride adduct byproduct is formed in less than 0.5 mol % based on the number of moles of fluorinated vinyl ether.

3. The process according to claim 1 further comprising collecting the fluorinated vinyl ether.

4. The process according to claim 1 wherein the metal carbonate is sodium carbonate or potassium carbonate.

5. The process according to claim 1 further comprising optimizing fluorinated vinyl ether yields by adjusting a variable selected from a feed rate of the propionyl fluoride, metal carbonate, a reaction temperature, a rate of stirring, or combinations thereof.

6. The process according to claim 1 further comprising recycling the unreacted 2-alkoxypropionyl fluoride from the stirred bed reactor.

7. The process according to claim 1 wherein the 2-alkoxypropionyl fluoride is given by the general formula X—(O—Y)$_a$—O—CF($CF_3$)COF wherein X is selected from the group consisting of $C_nF_{2n+1}$ wherein n is 1 to 10, $FSO_2(C_mF_{2m})$ wherein m is 1 to 10, and $FCO(C_dF_{2d})$ wherein d is 1 to 10; Y is selected from the group consisting of $C_pF_{2p}$ wherein p is 1 to 10, and $CF(CF_3)CF_2$; and a is 0 to 10.

8. The process according to claim 7 wherein the 2-alkoxypropionyl fluoride is selected from $CF_3$—O—CF($CF_3$)COF; $CF_3CF_2$—O—CF($CF_3$)COF; $CF_3CF_2CF_2$—O—CF($CF_3$)COF; $CF_3$—O—$CF_2CF_2CF_2$—O—CF($CF_3$)COF; $CF_3CF_2$—O—$CF_2$—O—CF($CF_3$)COF; $CF_3$—O—$CF_2CF_2$—O—$CF_2CF_2$—O—CF($CF_3$)COF; $CF_3CF_2$—O—$CF_2CF_2$—O—$CF_2CF_2$—O—CF($CF_3$)COF; $CF_3CF_2CF_2$—O—[CF($CF_3$)$CF_2$—O]$_a$CF($CF_3$)COF; $FSO_2CF_2CF_2CF_2CF_2$—O—CF($CF_3$)COF; or $FCOCF_2CF_2CF_2CF_2$—O—CF($CF_3$)COF.

9. The process according to claim 7 wherein the fluorinated vinyl ether is selected from $CF_3$—O—CF=$CF_2$; $CF_3CF_2$—O—CF=$CF_2$; $CF_3CF_2CF_2$—O—CF=$CF_2$; $CF_3$—O—$CF_2CF_2CF_2$—O—CF=$CF_2$; $CF_3CF_2$—O—$CF_2$—O—CF=$CF_2$; $CF_3$—O—$CF_2CF_2$—O—$CF_2CF_2$—O—CF=$CF_2$; $CF_3CF_2$—O—$CF_2CF_2$—O—$CF_2CF_2$—O—CF=$CF_2$; $CF_3CF_2CF_2$—O—[CF($CF_3$)$CF_2$—O]$_a$CF=$CF_2$; $FSO_2CF_2CF_2CF_2CF_2$—O—CF=$CF_2$; or $CH_3OCOCF_2CF_2CF_2CF_2$—O—CF=$CF_2$.

10. The process according to claim 1 wherein the metal carbonate is a powdered metal carbonate.

11. The process according to claim 1 further comprising heating the carbonate at 250° C. while flowing an inert gas over the metal carbonate for at least 2 hours.

12. The process according to claim 1 further comprising adjusting the feed rate of the 2-alkoxypropionyl fluoride to a working feed rate, wherein the working feed rate is the rate at which 95 mol % of the 2-alkoxypropionyl fluoride is converted to the fluorinated vinyl ether.

13. The process according to claim 1 wherein the 2-alkoxypropionyl fluoride is a liquid under atmospheric conditions.

14. The process according to claim 5 wherein the rate of stirring is adjusted so as to continuously expose unreacted metal carbonate to the 2-alkoxypropionyl fluoride.

15. The process according to claim 5 wherein the metal carbonate is selected to maximize conversion of the 2-alkoxypropionyl fluoride to the fluorinated vinyl ether.

16. The process according to claim 1 further comprising isolating a desired fluorinated vinyl ether from impurities.

17. The process according to claim 1 wherein the 2-alkoxypropionyl fluoride is $CF_3$—O—$CF_2CF_2CF_2$—O—CF($CF_3$)COF.

18. The process according to claim 1 wherein the fluorinated vinyl ether is $CF_3$—O—$CF_2CF_2CF_2$—O—CF=$CF_2$.

19. The process according to claim 1 wherein the 2-alkoxypropionyl fluoride is $CF_3CF_2$—O—$CF_2$—O—CF($CF_3$)COF.

20. The process according to claim 1 wherein the fluorinated vinyl ether is $CF_3CF_2$—O—$CF_2$—O—CF=$CF_2$.

21. The process according to claim 1 wherein the 2-alkoxypropionyl fluoride is $FSO_2CF_2CF_2CF_2CF_2$—O—CF($CF_3$)COF.

22. The process according to claim 1 wherein the fluorinated vinyl ether is $FSO_2CF_2CF_2CF_2CF_2$—O—CF=$CF_2$.

* * * * *

UNITED STATES PATENT AND TRADEMARK OFFICE
CERTIFICATE OF CORRECTION

PATENT NO. : 7,176,331 B2
APPLICATION NO. : 11/171966
DATED : February 13, 2007
INVENTOR(S) : Miguel A. Guerra It is certified that error appears in the above-identified patent and that said Letters Patent is hereby corrected as shown below:

Column 3
Line 32, delete "$C_2F_{2n+1}$" and insert -- $C_nF_{2n+1}$ -- in place thereof.

Column 5
Line 40, delete "Apply" and insert -- Apple -- in place thereof.
Line 47, delete "Perfluoromethoxypropoxyproponyl" and insert
-- Perfluoromethoxypropoxypropionyl -- in place thereof.
Lines 55-56, delete "perfluoromethoxypropoxyproponyl" and insert
-- perfluoromethoxypropoxypropionyl -- in place thereof.

Column 6
Line 25, delete "$FSO_2CF2CF_2CF_2CF_2$" and insert -- $FSO_2CF_2CF_2CF_2CF_2$ -- in place thereof.
Line 29, delete "$FSO_2CF2CF_2CF_2CF_2$" and insert -- $FSO_2CF_2CF_2CF_2CF_2$ -- in place thereof.
Line 42, delete "$FSO_2CF2CF_2CF_2CF_2$" and insert -- $FSO_2CF_2CF_2CF_2CF_2$ -- in place thereof.
Lines 56-57, delete "perfluoromethoxypropoxyproponyl" and insert
-- perfluoromethoxypropoxypropionyl -- in place thereof.

Column 7
Lines 8-9, delete "perfluoromethoxypropoxyproponyl" and insert
-- perfluoromethoxypropoxypropionyl -- in place thereof.

UNITED STATES PATENT AND TRADEMARK OFFICE
CERTIFICATE OF CORRECTION

PATENT NO.        : 7,176,331 B2
APPLICATION NO.   : 11/171966
DATED             : February 13, 2007
INVENTOR(S)       : Miguel A. Guerra It is certified that error appears in the above-identified patent and that said Letters Patent is hereby corrected as shown below:

<u>Column 8</u>
Lines 14-15, Claim 9, delete "$CF_3CF_2\!-\!O\!-\!CF_2\!-\!O\!-\!CF\!-\!CF_2;$" and insert
-- $CF_3CF_2\!-\!O\!-\!CF_2\!-\!O\!-\!CF\!=\!CF_2;$ -- in place thereof.

Signed and Sealed this

Fifteenth Day of May, 2007

JON W. DUDAS
*Director of the United States Patent and Trademark Office*